US010994116B2

(12) United States Patent
Donze et al.

(10) Patent No.: US 10,994,116 B2
(45) Date of Patent: May 4, 2021

(54) DRUG CARTRIDGE-BASED INFUSION PUMP (71) Applicant: BioQ Pharma Incorporated, San Francisco, CA (US)

(72) Inventors: Thomas T. Donze, San Bruno, CA (US); Ralph I. McNall, III, Belmont, CA (US); Joshua W. Kriesel, San Francisco, CA (US); Serena Joshi, San Francisco, CA (US)

(73) Assignee: BioQ Pharma Incorporated, San Francisco, CA (US)

( * ) Notice: Subject to any disclaimer, the term of this patent is extended or adjusted under 35 U.S.C. 154(b) by 297 days.

(21) Appl. No.: 16/024,763

(22) Filed: Jun. 30, 2018

(65) Prior Publication Data
US 2020/0001068 A1  Jan. 2, 2020

(51) Int. Cl.
A61M 39/18 (2006.01)
A61M 5/145 (2006.01)
A61M 39/20 (2006.01)
A61M 5/50 (2006.01)

(52) U.S. Cl.
CPC ........ A61M 39/18 (2013.01); A61M 5/14566 (2013.01); A61M 5/5086 (2013.01); A61M 39/20 (2013.01); A61M 2205/123 (2013.01)

(58) Field of Classification Search
CPC .............. A61M 39/18; A61M 5/14566; A61M 5/5086; A61M 39/20; A61M 2205/123; A61M 2005/3121; A61M 5/285; A61M 5/288; A61M 5/31501; A61M 5/3135; A61M 5/31513; A61M 5/31515; A61M 2005/3131; A61M 2205/12; A61M 5/14546
See application file for complete search history.

(56) References Cited

U.S. PATENT DOCUMENTS 3,909,910 A   10/1975  Rowe et al.
4,019,512 A    4/1977  Tenczar
4,137,913 A    2/1979  Georgi
4,861,335 A    8/1989  Reynolds
(Continued)

FOREIGN PATENT DOCUMENTS

WO      2011002853 A2    1/2011

Primary Examiner — Shefali D Patel
Assistant Examiner — Avery Smale
(74) Attorney, Agent, or Firm — Thomas W. Galvani, P.C.; Thomas W. Galvani (57) ABSTRACT An infusion pump includes a reusable housing unit, a disposable reservoir, and a cap fit on the reservoir, wherein the cap includes a conduit for fluid communication. An aseptic connector assembly includes first and second occlusions in the reservoir and the cap. A pull assembly extends from the aseptic connector assembly and forms the first and second occlusions. The pump has three states. In a storage state, the reservoir is separate from the housing unit and the first and second occlusions cooperate to occlude a wet path extending from the reservoir through the conduit in the cap. In a ready state, the reservoir is applied to the housing unit but the wet path is still occluded. In a use state, the reservoir is applied to the housing unit, the first and second occlusions are removed from the aseptic connector assembly, and the wet path is opened for communication.

20 Claims, 9 Drawing Sheets

(56) References Cited

U.S. PATENT DOCUMENTS

| | | | |
|---|---|---|---|
| 5,244,463 | A | 9/1993 | Cordner et al. |
| 5,324,258 | A | 6/1994 | Rohrbough |
| 5,906,589 | A | 5/1999 | Gordon et al. |
| 6,109,895 | A | 8/2000 | Ray et al. |
| 6,835,049 | B2 | 12/2004 | Ray |
| 7,169,128 | B2 | 1/2007 | Kriesel et al. |
| 7,220,244 | B2 | 5/2007 | Kriesel |
| 7,220,245 | B2 | 5/2007 | Kriesel |
| 7,316,245 | B2 | 1/2008 | Bivin |
| 7,470,253 | B2 | 12/2008 | Kriesel et al. |
| 7,481,244 | B2 | 1/2009 | Bivin |
| 7,513,273 | B2 | 4/2009 | Bivin |
| 7,694,938 | B2 | 4/2010 | Kriesel et al. |
| 7,735,522 | B2 | 6/2010 | Bivin et al. |
| 7,776,006 | B2 | 8/2010 | Childers et al. |
| 7,789,853 | B2 | 9/2010 | Kriesel |
| 7,828,770 | B2 | 11/2010 | Bivin et al. |
| 7,828,772 | B2 | 11/2010 | Kriesel et al. |
| 7,833,195 | B2 | 11/2010 | Kriesel et al. |
| 7,837,653 | B2 | 11/2010 | Kriesel et al. |
| 7,896,843 | B2 | 3/2011 | Kriesel et al. |
| D636,271 | S | 4/2011 | Kriesel |
| 7,993,304 | B2 | 8/2011 | Kriesel et al. |
| 8,029,468 | B2 | 10/2011 | Kriesel et al. |
| 8,057,435 | B2 | 11/2011 | Kriesel et al. |
| 8,083,503 | B2 | 12/2011 | Voltenburg, Jr. et al. |
| 8,083,717 | B2 | 12/2011 | Kriesel |
| 8,100,890 | B2 | 1/2012 | Kriesel et al. |
| 8,105,280 | B2 | 1/2012 | Iddan et al. |
| 8,114,052 | B2 | 2/2012 | Bivin et al. |
| 8,123,723 | B2 | 2/2012 | Bivin et al. |
| 8,133,204 | B1 | 3/2012 | Kriesel |
| 8,142,398 | B1 | 3/2012 | Kriesel et al. |
| 8,197,445 | B2 | 6/2012 | Kriesel et al. |
| 8,211,059 | B2 | 7/2012 | Kriesel et al. |
| 8,226,609 | B2 | 7/2012 | Kriesel et al. |
| 8,231,575 | B2 | 7/2012 | Kriesel |
| 8,287,521 | B2 | 10/2012 | Kriesel et al. |
| 8,292,848 | B2 | 10/2012 | Kriesel et al. |
| 8,292,876 | B2 | 10/2012 | Kriesel et al. |
| 8,317,753 | B2 | 11/2012 | Kriesel et al. |
| 8,361,009 | B2 | 1/2013 | Lee et al. |
| 8,377,043 | B2 | 2/2013 | Kriesel et al. |
| 8,388,571 | B2 | 3/2013 | Joshi et al. |
| 8,388,578 | B2 | 3/2013 | Joshi et al. |
| 8,403,887 | B2 | 3/2013 | Kriesel et al. |
| 8,480,656 | B2 | 7/2013 | Kriesel |
| 8,622,965 | B2 | 1/2014 | Kriesel |
| 8,672,885 | B2 | 3/2014 | Kriesel et al. |
| 8,821,454 | B2 | 9/2014 | Kriesel et al. |
| 2002/0017296 | A1* | 2/2002 | Hickle .............. A61M 16/0093 128/203.12 |
| 2003/0030272 | A1* | 2/2003 | Johnson ................ A61M 39/18 285/3 |
| 2005/0020980 | A1* | 1/2005 | Inoue .................... A61M 39/10 604/152 |
| 2005/0119620 | A1* | 6/2005 | Tachikawa ........ A61M 5/31501 604/187 |
| 2005/0151105 | A1 | 7/2005 | Ryan et al. |
| 2006/0030838 | A1 | 2/2006 | Gonnelli |
| 2006/0052322 | A1 | 3/2006 | Roth et al. |
| 2007/0235083 | A1 | 10/2007 | Glugos |
| 2009/0093793 | A1 | 4/2009 | Gross et al. |
| 2009/0124994 | A1 | 5/2009 | Roe |
| 2011/0282284 | A1 | 11/2011 | Kriesel et al. |
| 2011/0282300 | A1 | 11/2011 | Kriesel et al. |
| 2012/0130341 | A1 | 5/2012 | Whitley |
| 2013/0014856 | A1 | 1/2013 | Young |
| 2013/0218123 | A1 | 8/2013 | Beiriger |
| 2013/0296792 | A1 | 11/2013 | Cabiri |
| 2013/0296803 | A1 | 11/2013 | Kriesel |
| 2013/0331823 | A1 | 12/2013 | Askem et al. |
| 2014/0058318 | A1 | 2/2014 | Yodfat et al. |
| 2014/0213975 | A1 | 7/2014 | Clemente et al. |
| 2014/0241923 | A1 | 8/2014 | Nzike et al. |
| 2014/0296787 | A1 | 10/2014 | Agard et al. |
| 2014/0301913 | A1 | 10/2014 | Williams et al. |
| 2014/0318995 | A1 | 10/2014 | Eiltertsen |
| 2015/0174304 | A1 | 6/2015 | Askem et al. |
| 2015/0209505 | A1* | 7/2015 | Hanson .............. A61M 5/14566 604/135 |
| 2016/0144094 | A1 | 5/2016 | Margolin et al. |
| 2016/0199568 | A1* | 7/2016 | McNall, III ...... A61M 5/14232 604/67 |
| 2016/0250411 | A1 | 9/2016 | Nesse et al. |
| 2017/0232187 | A1 | 8/2017 | McNall et al. |

* cited by examiner

DRUG CARTRIDGE-BASED INFUSION PUMP

FIELD OF THE INVENTION

The present invention relates generally to medical equipment, and more particularly to devices for dispensing drugs to a patient.

BACKGROUND OF THE INVENTION

Precise infusion of volumes of liquid drug or medicament through an administration line is usually accomplished by an infusion pump. Traditional infusion pumps make use of a flexible infusion bag suspended above the patient. For many medicaments and drugs, a pharmacist, nurse, doctor, or other medical professional is required to attach and couple the bag to the pump, making connections between the two which may be contaminated. This can involve wrapping a tubing line around a peristaltic pump, mixing or diluting drugs, connecting fittings, and other activities which are susceptible to medication errors and contamination risks. Other problems exist with conventional pumps. For example, periodic monitoring of the apparatus by a nurse, doctor, or other medical professional is required to detect malfunctions of the infusion pump.

Accordingly, over the years, infusion pumps developed into increasingly more complex devices of great expense and sophistication. Such devices include a large number of features, options, and programmability possibilities. While those capabilities can be advantageous in providing a range of customization to medicament administration, they also lead to user error and the possibility of patient harm, injury, or death.

Complicated infusion pumps also typically require many time-consuming steps for setup. Increased preparation requirements increase the risk of contaminating the pump, the medicament reservoir, the administration line, or other elements of the intravenous line system, posing a hazard to the patient. An improved system for providing a convenient, reliable, accurate, and sterile infusion of liquid medicament is needed.

SUMMARY OF THE INVENTION

An infusion pump includes a reusable housing unit, a disposable reservoir, and a cap fit on the reservoir, wherein the cap includes a conduit for fluid communication. An aseptic connector assembly includes first and second occlusions in the reservoir and the cap. A pull assembly extends from the aseptic connector assembly where it forms the first and second occlusions. The pump has three states. In a storage state, the reservoir is separate from the housing unit and the first and second occlusions cooperate to occlude a wet path extending from the reservoir through the conduit in the cap. In a ready state, the reservoir is applied to the housing unit but the wet path is still occluded. In a use state, the reservoir is applied to the housing unit, the first and second occlusions are removed from the aseptic connector assembly, and the wet path is opened for communication.

The above provides the reader with a very brief summary of some embodiments discussed below. Simplifications and omissions are made, and the summary is not intended to limit or define in any way the scope of the invention or key aspects thereof. Rather, this brief summary merely introduces the reader to some aspects of the invention in preparation for the detailed description that follows.

BRIEF DESCRIPTION OF THE DRAWINGS

Referring to the drawings.

DETAILED DESCRIPTION

Figure 1A:
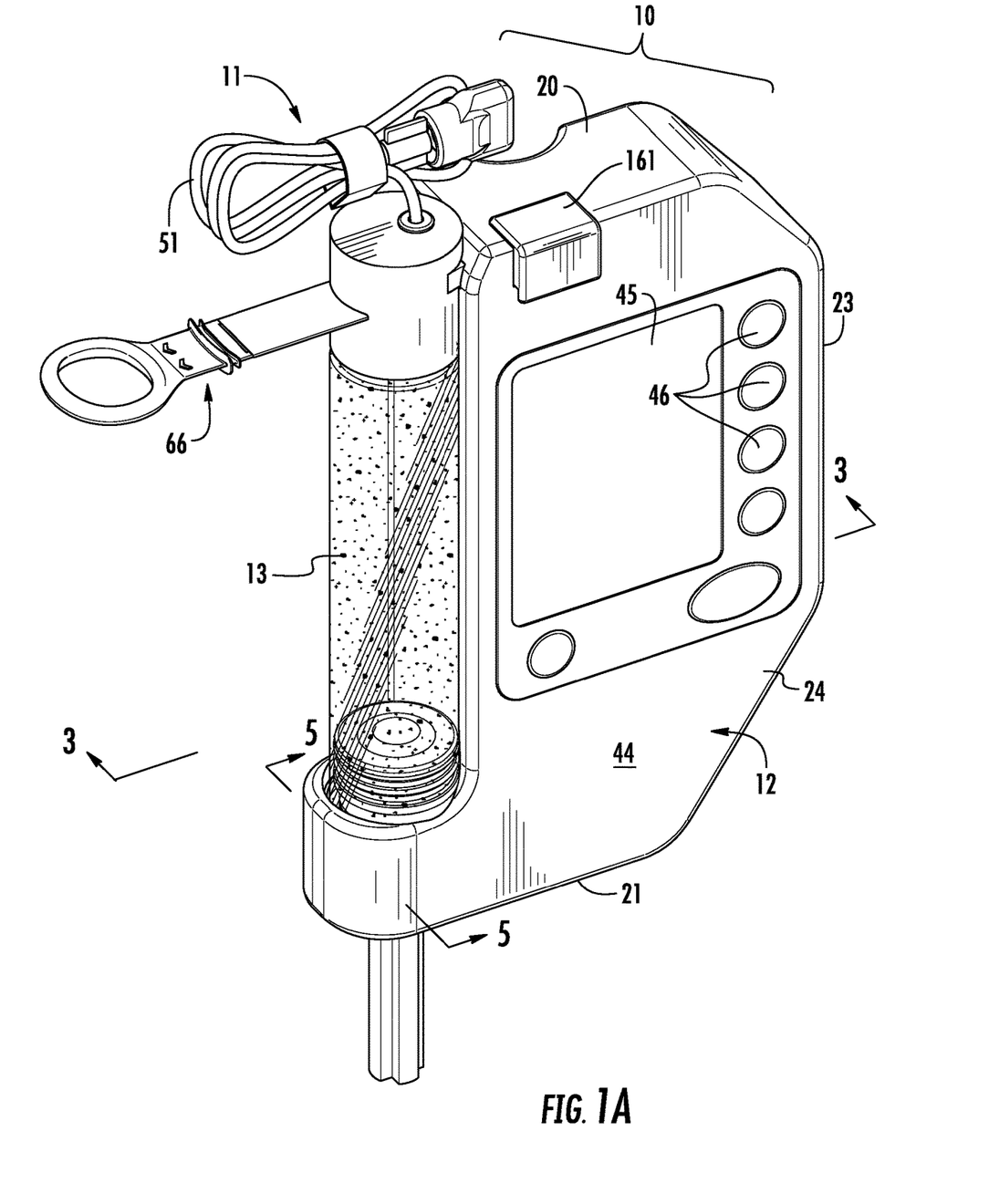
FIG. 1A is front perspective view of a drug cartridge-based infusion pump having a cartridge applied to a housing unit, illustrating the pump in a ready state in which the cartridge is applied to the housing unit.
Figure 1B:
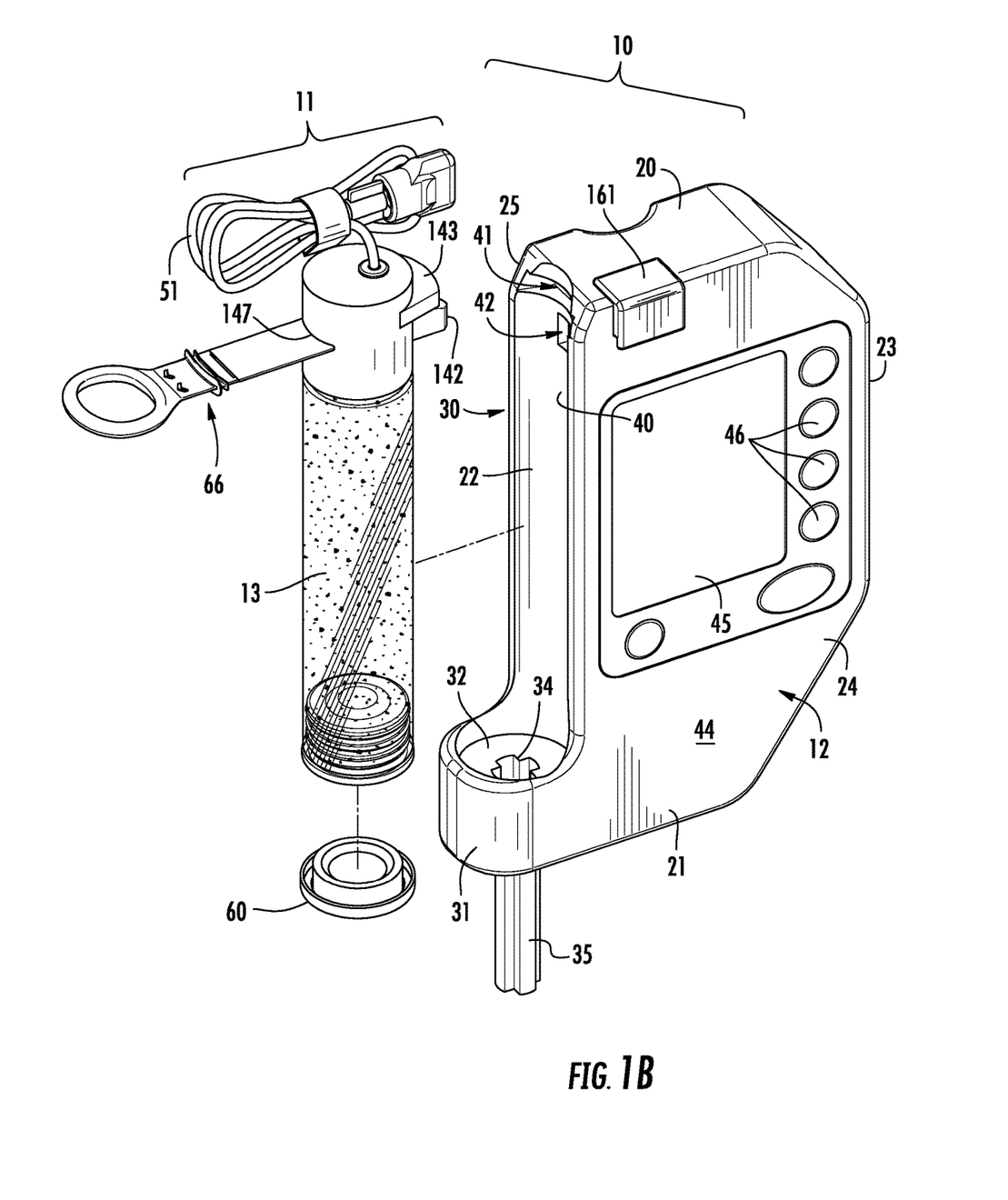
FIG. 1B illustrates the pump of FIG. 1A in a storage state, with the cartridge free of the housing unit.

Reference now is made to the drawings, in which the same reference characters are used throughout the different figures to designate the same elements. FIGS. 1A and 1B are front perspective views illustrating, respectively, a drug cartridge-based infusion pump 10 (hereinafter, "pump 10") in a ready state in which a drug cartridge 11 is applied to a housing unit 12, and a storage state in which the cartridge 11 is separate from the housing unit 12. The pump 10 is useful for holding and delivering a quantity of fluid medicament 13 to a patient via an administration line, and its structure and operation mitigate opportunities to introduce contamination into an intravenous line system. The pump 10 uniquely combines a reusable housing unit 12 with disposable cartridges 11 without sacrificing sterility concerns. The medicament 13 in the drug cartridge 11 may be any medicament in fluid form, including high-concentrate drugs, low-concentrate drugs, saline solution, and other liquids or fluids. The cartridge 11 is always fluidically isolated from the housing unit 12, meaning that cartridge 11 is closed to fluid communication with the housing unit 12, the fluid in the cartridge 11 never touches any part of the housing unit 12, and no part of the housing unit 12 contacts the fluid in the cartridge 11.

The housing unit 12 is constructed from a durable, rigid plastic, either in a monolithic construction or from several pieces coupled together by snap tab fittings, adhesive, sonic welding, screws, or like fastening methods suitable for an assembled medical enclosure. The embodiment shown throughout these drawings is a preferred, yet not limiting embodiment, and it should be understood that variations in the design of various structural elements—such as the housing unit 12—do not alter the principle operation of the pump 10. The housing unit 12 is a generally hollow body having a top 20, an opposed bottom 21, opposed sides 22 and 23, and a front and back 24 and 25.

The housing unit 12 includes a dock 30 at the side 22. The dock 30 is a receptacle for receipt of the cartridge 11. At the bottom 21, the dock 30 has a quasi-cylindrical laterally-projecting foot 31. The top of the foot 31 is recessed and defines a seat 32 with a hollow bore 34. A plunger rod 35 carried in the housing unit 12 at the foot 31 is coupled to a motor within the housing unit 12 and mounted for reciprocal movement through the bore 34. The plunger rod 35 drives a plunger within the cartridge 11 to dispense medicament.

A hold 40 extends up from the foot 31 along the side 22. The hold 40 is a semi-cylindrical recess into the housing unit 12 and is sized and shaped to closely receive the cartridge 11 when applied to the housing unit 12. Capture mechanisms at the top of the dock 30 secure the cartridge 11 when applied to the housing unit 12. There is a slot 41 in the hold 40 proximate the top 20 of the housing unit 12 that receives part of the cartridge 11, and just below is a smaller slot 42. Inside this smaller slot 42 is a tab 43, shown best in FIG. 3B, which has an enlarged head for snapping into a catch extending from the cartridge 11, as is described in more detail below.

Figure 3A:
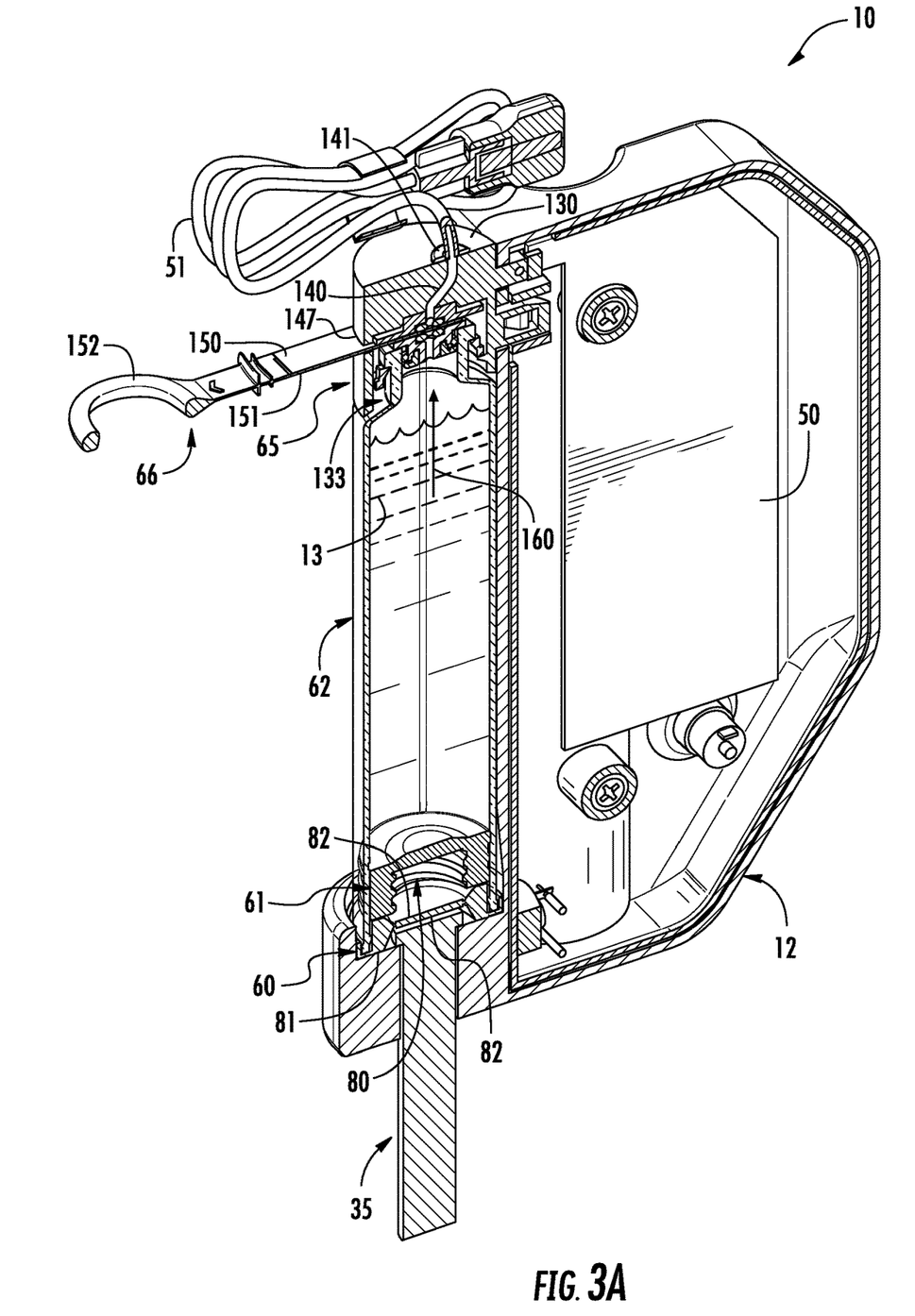
FIG. 3A is a section view taken along the line 3-3 in FIG. 1A, showing the pump in the ready state.

Returning to FIGS. 1A and 1B, the housing unit 12 has a wide face 44 into which is set a display 45 and a plurality of control buttons 46. The display 45 and buttons 46 are carried on and operatively coupled to a printed circuit board 50 (hereinafter, "PCB 50") within the housing unit 12, as shown in FIG. 3A. Depressing the buttons 46 provides signals to the PCB 50, which controls operation of the pump 10.

Figure 2:
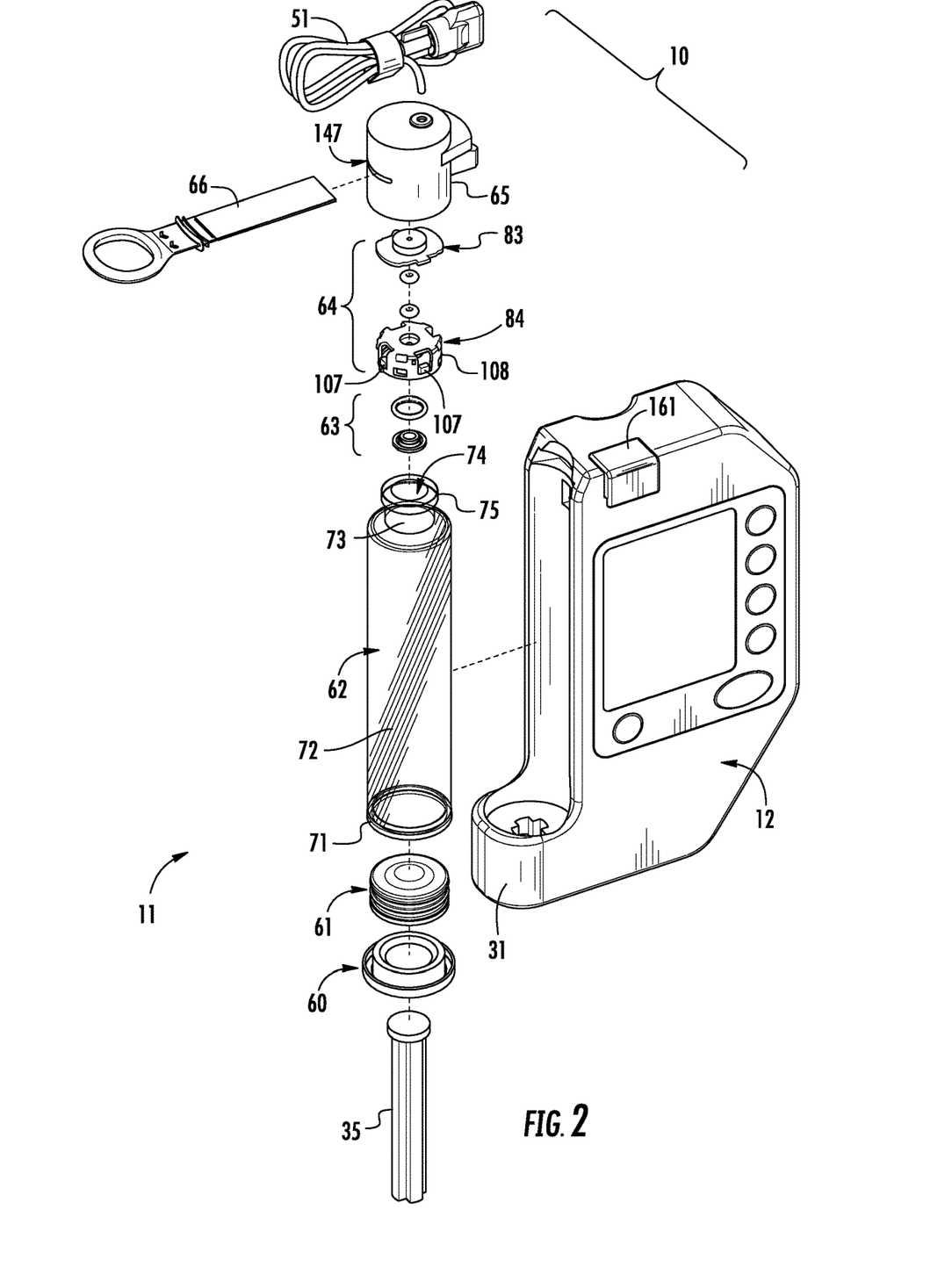
FIG. 2 is a front perspective view of the pump of FIG. 1A in which the cartridge is shown in exploded format.

FIGS. 1B and 2 illustrate the cartridge 11 separate from the housing unit 12 and in an exploded format. The cartridge 11 includes a tamper-evident base 60, a plunger 61, a reservoir 62, a seal assembly 63, an aseptic connector assembly 64, a cap 65, and a pull assembly 66. Also shown is an administration line above the cartridge 11 and the plunger rod 35 below the cartridge 11, but these are not part of the cartridge 11.

The reservoir 62 is a rigid cylinder, such as a syringe barrel. It has an open top 70, an open bottom 71, and a transparent cylindrical sidewall 72 extending therebetween. Proximate to the top 70 of the reservoir 62, the sidewall narrows into a neck 73 which terminates in a mouth 75. The sidewall has an annular flange at the mouth 75 defining a lip 74 which bounds the mouth 75. The neck 73 and lip 74 are formed integrally and monolithically as part of the sidewall 72.

The plunger 61 is mounted for movement within the reservoir 62. The plunger 61 is constructed of a material or combination of materials having resilient material characteristic, and has an outer diameter just slightly greater than an inner diameter of the reservoir 62, so that the plunger 61 is slightly radially compressed when disposed within the reservoir 62. The plunger 61 forms an impermeable seal against the reservoir 62, so that the medicament 13 contained within the reservoir 62 cannot and does not leak from the reservoir 62. As seen in FIG. 3A, the plunger 61 includes a recessed socket 80 extending into the plunger 61 from the bottom.

Just below the plunger 61 is the tamper-evident base 60 (hereinafter, "base 60"). Referring to FIG. 3A, the base 60 is a rigid outer ring 81 with a frangible central barrier 82. The outer ring 81 is annular and projects upwardly to a top and downwardly to a bottom with respect to the central barrier 82, disposed at an intermediate location between the top and bottom of the outer ring 81. For purposes of clarity, words like "top," "bottom," "up," "down," "above," "below," "higher," and "lower" are used to indicate location, orientation, or relative arrangement of parts of the pump 10, considering the top 20 is preferably at the top and the bottom 21 is preferably at the bottom when the pump 10 is oriented in a preferred manner. The central barrier 82 spans within the outer ring 81 and is formed to the outer ring 81 continuously around the inside of the outer ring 81 with a thinned annulus. The central barrier 82 is thus frangible and can be torn or severed from the outer ring 81 when the plunger rod 35 advances through the base 81. The outer diameter of the base 60 corresponds in size to the inner diameter of the reservoir 62, so that the base 60 is snug fit inside the reservoir 62 at the bottom 71 of the reservoir 62. Indeed, when the plunger rod 35 does advance through the base 60, the central barrier rod 82 tears away from the outer ring 81, which remains in place at the bottom 71 of the reservoir 62.

Figure 3B:
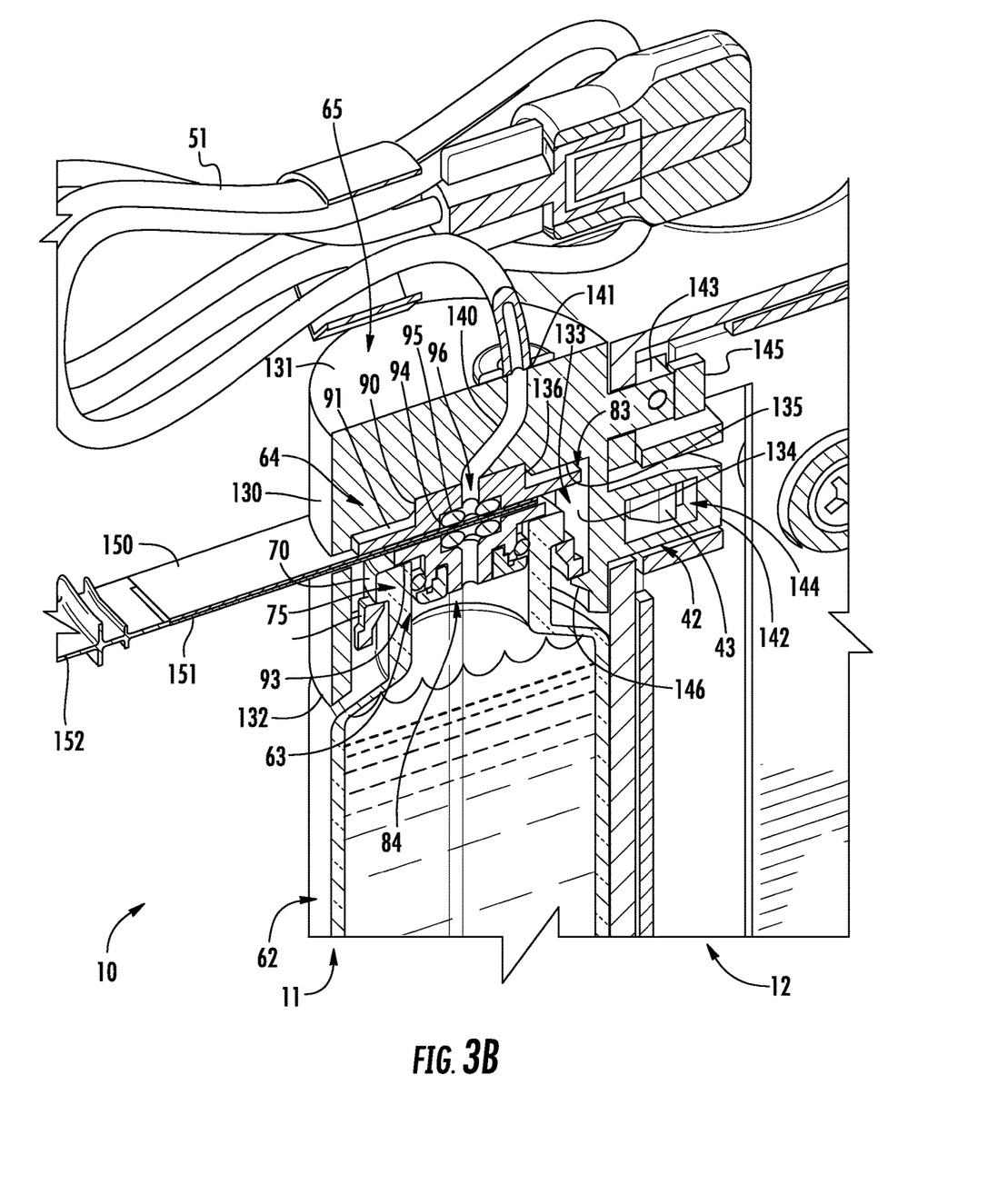
FIGS. 3B and 3C are identical enlarged section views taken along the line 3-3 in FIG. 1A, showing the pump in the ready state.

Turning now to FIG. 3B, which illustrates an enlarged portion of FIG. 3A, the top 70 of the reservoir 62, the seal assembly 63, the aseptic connector assembly 64, and the cap 65 are shown. The aseptic connector assembly 64 is snug fit over the mouth 75 of the reservoir 62 and is held there to define a pathway from the reservoir 62 in communication with a conduit formed internally in the cap 65. The aseptic connector assembly 64 includes a first portion, or upper aseptic connector 83, and an opposed separate second portion, or lower aseptic connector 84.

Referring still to FIG. 3B, the upper aseptic connector 83 includes a wide, squat, cylindrical base 90 having a top and bottom, and a wide oval flange 91 extending radially outward from the base 90. The flange 91 is shorter than the base 90 at approximately one-fourth the height of the base 90. The base 90 and flange 91 cooperate to define a flat lower surface 93 of the upper aseptic connector 83 extending across both the base 90 and the flange 91. Extending upward into the base 90 from the lower surface 93 is a seat 94. The seat 94 is a cylindrical depression in the upper aseptic connector 83 and receives a first annular gasket 95 therein. The depth of the seat 94 is slightly less than the height of the gasket 95 so that the gasket 95 protrudes slightly beyond the lower surface 93 of the upper aseptic connector 83 when received in the seat 94. The gasket 95 is constructed of a material or combination of materials having characteristics of inertness, low permeability, durability, and compressibility, such as rubber. The seat 94 is located in the upper aseptic connector 83 concentric to both the base 90 and the flange 91. An axial bore 96 extends centrally and coaxially through the upper aseptic connector 83 from the seat 94 upward to the top of the upper aseptic connector 83. The bore 96 provides a pathway for movement of fluid through the upper aseptic connector 83.

Figure 3C:
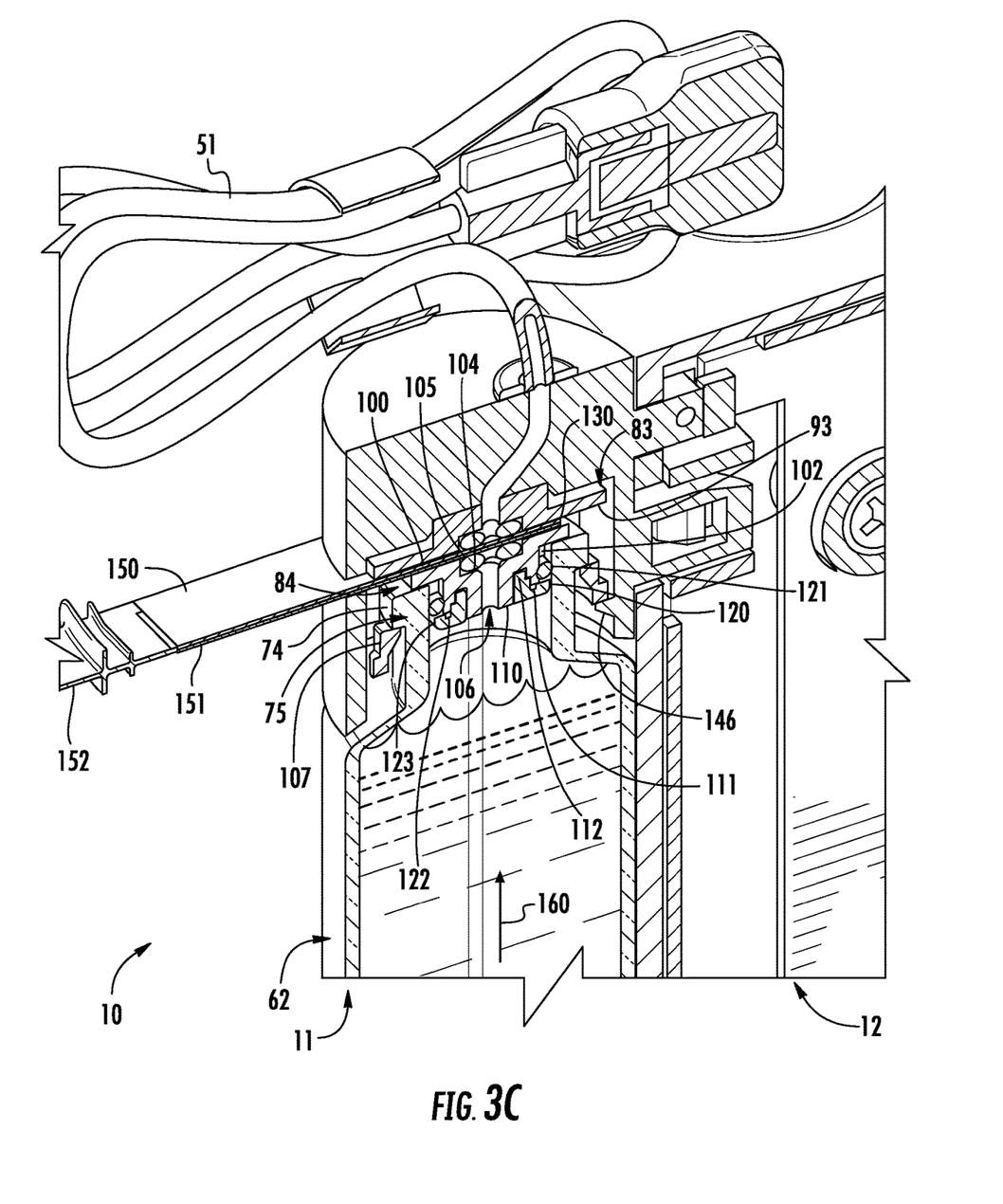

The lower aseptic connector 84 is somewhat similar to the upper aseptic connector 83. Referring to FIG. 3C, which is an identical view to FIG. 3B presented again to reduce the density of reference characters, the lower aseptic connector 84 includes a top 100, a bottom 101, and a perforated cylindrical sidewall 102 extending from the top 100 to the bottom 101. The top 100 has a flat upper surface 103, which is pressed toward the flat lower surface 93 of the upper aseptic connector 83. A seat 104 extends downward into the top 100 of the lower aseptic connector 84 from upper face 103; the seat 104 is a cylindrical depression which receives a second annular gasket 105 therein. The depth of the seat 104 is slightly less than the height of the gasket 105 so that the gasket 105 protrudes slightly beyond the upper surface 103 when the gasket 105 is received in the seat 104. The gasket 105 is constructed of a material or combination of materials having characteristics of inertness, low permeability, durability, and compressibility, such as rubber. The seat 104 is concentric to the sidewall 102. A post 110 extends downward from the top 100 and is formed integrally thereto. The post 110 surrounds a bore 106 which extends centrally and coaxially through the lower aseptic connector 84 from the seat 104 downward to the bottom of the post 110 disposed inside the neck 73 of the reservoir 62. The bore 106 provides a pathway for movement of fluid through the lower aseptic connector 84. This bore 106 provides a pathway for the movement of fluid out of the reservoir 62 through the lower aseptic connector 84. A short, annular collar 111 surrounds the post 110. The collar 111 is radially spaced apart from the post 110 and, as such, defines a small annular gap 112 therebetween.

The lower aseptic connector 84 caps the reservoir 62. With continuing reference to FIG. 3C, the lower aseptic connector 84 is fit into the reservoir 62 at the mouth and is sealed to it by the seal assembly 63 of a washer 120 and a gasket 121. The washer 120 has an annular structure, a central bore defining a constant inner diameter, and a stepped outer diameter. The outer diameter increases in discrete amounts from the top of the washer 120 to the bottom. This stepped outer diameter engages with a stepped inner diameter of the collar 111 surrounding the post 110 of the lower aseptic connector 84. The washer 120 includes an annular channel 122 bound on the inside by the stepped outer diameter and bound on the outside by a low upstanding annular lip 123 at the periphery of the washer 120. The annular channel 122 is open upward.

The gasket 121 surrounds the collar 111, just above the lip 123 at the periphery of the washer 120. The seal assembly 63 cooperates with the lower aseptic connector 84 to close and seal the reservoir 62. During assembly of the pump 10, the gasket 121 is placed around the collar 111 of the lower aseptic connector 84, proximate to its bottom. The washer 120 is then introduced to the gap 112 defined between the post 110 and the collar 111. Preferably, the lower aseptic connector 84 is disposed in the mouth 75, and the gasket 121 is between the collar 111 and the inner surface of the reservoir 62 at the mouth 75. Tabs 107 on the lower aseptic connector 84 are directed inwardly and latch under the lip at the top of the reservoir 62, thereby holding the lower aseptic connector 84 in place with respect to the reservoir 62. The washer 120 acts in part as a shim, and as it is introduced and advanced into the gap 112, it forces the collar 111 radially outward. This compresses the gasket 121 between the collar 111 and the reservoir 62, thereby forming a fluid impervious seal. The washer 120 is advanced into the gap 112 until the bottom edge of the collar 111 is seated in the channel 122 inboard of the lip 123, as shown in FIG. 3C.

The lower aseptic connector 84 cooperates with the seal assembly 63 to seal the reservoir 62. The cap 65 fits over the lower aseptic connector 84 to hold the upper and lower aseptic connectors 83 and 84 in compressive contact against each other, and to hold the cartridge 11 in the housing unit 12.

Referring now to FIGS. 3A and 3B, the cap 65 has a cylindrical solid body 130 with a closed top 131 and an open bottom 132. The open bottom 132 leads to an interior recess or cavity 133 extending upward into the cap 65 from the bottom 132. The cavity 133 is defined by a cylindrical inner surface 134 and an upper surface 135 thereof. A short central depression 136 is recessed upwardly into the body 130 from the upper surface 135; the depth of this depression 136 into the body 130 corresponds to the height of the base 90 above the flange 91 on the upper aseptic connector 83. The base 90 of the upper aseptic connector 83 is snug fit and glued into this depression 136.

An internal conduit 140 extends from an opening at the upper surface 135 of the cavity 133 to an outlet 141 at the top 131 of the cap 65. The conduit 140 couples the bore 96 of the upper aseptic connector 83 with the outlet 141. Typically, the outlet 141 will be connected to the administration line 51 for connection to a patient or to other parts of an intravenous line system.

The cap 65 also includes a catch 142 and a sensor 143, each extending laterally from the side of the cap 65. The catch 142 is an integral and rigid projection of the cap 65 to the side and is formed with a slot 144 extending transversely through the catch 142. The slot 144 is sized to receive the tab 43 in the housing unit 12; when the tab 43 slips into the slot 144, the enlarged head of the tab 43 becomes latched on the catch 142, thereby preventing inadvertent removal of the cartridge 11 from the housing unit 12. The sensor 143 is an infrared, NFC, or other sensor type on the cap 65, which is brought into proximity to a reader 145 on the PCB 50 when the cartridge 11 is applied to the housing unit 12. The sensor 143 corresponds to the reservoir 62; the sensor 143 carries information about the reservoir 62 and the medicament 13 it contains. The reader 145 is electrically coupled to a logic controller on the PCB 50, so that the sensor 143 is coupled in data communication with the PCB 50 in the housing unit 12 when the pump 10 is in ready and use states. The sensor 143 conveys information to the reader 145, allowing the PCB 50 to determine information about the cartridge 11, such as medicament type, volume, date of creation, date of expiration, etc.

The pull assembly 66 is a two-ply ribbon structure fitted with a pull ring. With reference to FIGS. 3A and 3B, the pull assembly extends from within the aseptic connector assembly 64, where it is disposed between the upper and lower aseptic connectors 83 and 84, forms the first and occlusions, and occludes both the upper and lower aseptic connectors 83 and 84, to outside the reservoir 62 and the cap 65. The pull assembly 66 includes a first or upper ribbon 150, a second or lower ribbon 151, and a pull ring 152 secured on the free ends of the upper and lower ribbons 150 and 151.

The upper ribbon 150 is a flexible, thin film, or is constructed from flexible, thin films. Within the aseptic connector assembly 64, the upper ribbon 150 overlies the bore 96, the gasket 95, and a portion of the lower surface 93 surrounding the gasket 95. The upper ribbon 150 has an upper surface and an opposed lower surface. In the aseptic connector assembly 64, the upper ribbon 150 is folded over on itself: the upper and lower surfaces are against each other. A free end of the upper ribbon 150 then extends out away from the upper aseptic connector 83 to the pull ring 152, outside the cartridge 11. The upper surface of the upper ribbon 150 is adhered and sealed to the lower surface 93 of the upper aseptic connector 83 around the gasket 95, thereby forming a continuous, annular seal between the upper ribbon 150 and the lower surface 93 to act as an occlusion and a barrier to fluid migration. The upper ribbon 150 thus occludes the upper aseptic connector 83.

Similarly, the lower ribbon 151 is a flexible, thin film, or is constructed from flexible, thin films. Within the aseptic connector assembly 64 (shown more clearly in FIG. 3C), the lower ribbon 151 overlies the bore 106, the gasket 105, and a portion of the upper surface 103 surrounding the gasket 105. The lower ribbon 151 has an upper surface and an opposed lower surface. In the aseptic connector assembly 64, the lower ribbon 151 is folded over on itself: the upper and lower surfaces are against each other. A free end of the lower ribbon 151 then extends out away from the lower aseptic connector 84 to the pull ring 152, outside the cartridge 11. The lower surface of the lower ribbon 151 is adhered and sealed to the upper surface 103 of the lower aseptic connector 84 around the gasket 105, thereby forming a continuous, annular seal between the lower ribbon 151 and the upper surface 103 to act as an occlusion and a barrier to fluid migration. The lower ribbon 151 thus occludes the lower aseptic connector 84.

The upper ribbon 150 is characterized as a first occlusion of the aseptic connector assembly 64, and the lower ribbon 151 is characterized as a second occlusion of the aseptic connector assembly 64, meaning the upper and lower ribbons 150 and 151 prevent fluid communication through the aseptic connector assembly 64. The upper ribbon 150, being sealed only to the upper aseptic connector 83, is only an occlusion to the upper aseptic connector 83, and prevents fluid communication through the upper aseptic connector 83. The lower ribbon 151 is only an occlusion to the lower aseptic connector 84 because it is sealed only to the lower aseptic connector 84, and thus prevents fluid communication through the lower connector assembly 84 only. The occlusions are part of the aseptic connector assembly 64.

The upper and lower ribbons 150 and 151 extend out of the aseptic connector assembly 64. They are adhered, sonically welded, or otherwise fixed to each other at the pull ring 152, which is a rigid ring on the free ends of the upper and lower ribbons 150 and 151. The pull ring 152 allows a user to grasp and remove the pull assembly 66 from the cartridge 11 and from the aseptic connector assembly 64.

The upper and lower ribbons 150 and 151 allow independent, separate sterilization of the cap 65 and reservoir 62. During assembly of the cartridge 11, the upper aseptic connector 83 is applied to the cap 65. The base 90 of the upper aseptic connector 83 is registered with the depression 136 in the cap 65 and a small amount of adhesive is placed in the depression 136 before the base 90 is seated therein. The upper aseptic connector 83 is thus seated in the cap 65 with its bore 96 registered with the conduit 140. The gasket 95 is seated in the seat 94 of the upper aseptic connector 83, and the upper ribbon is placed over the gasket 95 and sealed to the lower surface 93 around it. The cap 65 is then sterilized, such as by Gamma- or ETO-sterilization or some other like medical sterilization process. The outlet 141 may be fitted with the administration line 51 or may be fitted with one later on.

The reservoir 62 is sterilized as well. As described above, the lower aseptic connector 84 is set into the mouth 75 of the reservoir 62 and sealed therein with the seal assembly 63. The reservoir 62 is then filled with medicament 13, and the plunger 61 is set into the reservoir 62, thereby sealing the other end of the reservoir 62. The medicament 13 is a fluid and is preferably one of the following fluids, but is not limited to acetaminophen, ketamine, propofol, dexmedetomidine, fentanyl, remifentanyl, etomidate, midazolam, foscarnet, ganciclovir, dopamine, dobutamine, milrinone, hemin, bupivacaine, ropivacaine, lidocaine, ciprofloxacin, cefazolin, fluconazole, cefmetazole, nafcillin, zoledronic acid, hetastarch, lactated ringers, hydroxyethyl startch, sodium chloride, dextrose, bendamustine, filgrastim, aztreonam, 5-fluorouracil, cetuximab, bortezomib, epirubicin, fludarabine, irinotecan, oxalaplatin, paclitaxel, carboplatin, cisplatin, cytarabine, methotrexate, vinblastine, vincristine, and ifosfamide. The base 60 is also fit over the bottom 71 of the reservoir 62 to indicate whether the reservoir 62 is or has been tampered. The lower ribbon 151 is then placed over the gasket 105 and sealed to the upper surface 103 around it. The reservoir 62 is then sterilized.

With the upper ribbon 150 occluding and sealing the upper aseptic connector 83 after sterilization and the lower ribbon 151 occluding and sealing the lower aseptic connector 84 after sterilization, the fluid-contacting portions of the cartridge 11 are maintained in a sterile state. The fluid-contacting portions of the cartridge 11 define a wet path 160 through the cartridge 11. This wet path 160, generally illustrated with an arrowed line in FIGS. 3A, 3B, and 3C, includes the plunger 61, the reservoir 62, the bore 106 and the gasket 105 in the lower aseptic connector 84, the bore 96 and the gasket 95 in the upper aseptic connector 83, and the conduit 140 in the cap 65, and the path that medicament 13 takes when being dispensed from the reservoir 62, pushed by the advancing plunger 61. The constituent structures of the wet path 160 are the only elements of the cartridge 11 which are in contact with the medicament 13. Indeed, the constituent structures of the wet path 160 are the only elements of the pump 10 which are ever in contact with the medicament 13. Since those structures are entirely contained within the cartridge 11, the cartridge 11 is always fluidically isolated from the housing unit 12; no fluid in the cartridge 11 ever contacts the housing unit 12.

Once the reservoir 62 and the cap 65 are sterilized separately, they can be brought together. The cap 65 is registered with the reservoir 62, the cavity 133 of the cap 65 is directed toward the top 70 of the reservoir 62 and the lower aseptic connector 84 thereon, and the cavity 133 is moved over the top 70 of the aseptic connector 84 until the upper and lower aseptic connectors 83 and 84 come into contact. The lower aseptic connector 84 is held in place on the reservoir 62 by the engagement of its tabs 107 with the lip 74 of the reservoir 62 and by the compression of the seal assembly 63 against the mouth 75 of the reservoir 62, and the upper aseptic connector assembly 83 is held in place by adherence to the upper surface 135 of the cap 65. When the cap 65 and reservoir 62 are registered in this manner, the gaskets 95 and 105 and the bores 96 and 106 are registered with each other as well. The upper and lower ribbons 150 and 151 are disposed in contact between the gaskets 95 and 105. The cap 65 is further advanced downward on the reservoir 62, thereby compressing the gaskets 95 and 105 toward each other with the upper and lower ribbons 150 and 151 therebetween, until the cap 65 locks onto the reservoir 62. The inner surface 134 of the cap 65 is formed with several inwardly-directed teeth 146 which pass into and catch just under the lower aseptic connector 84. The teeth 146, once engaged under the lower aseptic connector 84, cannot be disengaged without breaking the cap 65 or the lower aseptic connector 84. With the lower aseptic connector 84 secured on the reservoir 62, and the cap 65 secured on the lower aseptic connector 84, the upper and lower aseptic connectors 83 and 84 are thus held in compressive contact, maintained in coaxial alignment, so that when the pull assembly 66 is removed from the cartridge 11, the bores 96 and 106 can be joined to each other in fluid communication and the wet path 160 opened.

With the cap 65 secured on the reservoir 62, the free ends of the upper and lower ribbons 150 and 151 both loosely extend out of a slot 147 in the cap 65. The pull ring 152 is fit to the free ends of the upper and lower ribbons 150 and 151. The upper and lower ribbons 150 and 151 are straightened and flattened, so that the lower surface of the upper ribbon 150 is flat against the upper surface of the lower ribbon 151, and the pull ring 152 is then adhered, sonically welded, or otherwise fixed to the free ends of the upper and lower ribbons 150 and 151, thereby similarly fixing the upper and lower ribbons 150 and 151 to each other as well.

In this manner, the assembled cartridge 11 and the housing unit 12 are separate in a storage state of the pump 10. The storage state is shown most clearly in FIGS. 1B and 1s characterized in that the cartridge 11 is free of and fluidically isolated from the housing unit 12. The upper and lower ribbons 150 and 15 are disposed between the first and second gaskets 95 and 105. The occlusions of the upper and lower ribbons 150 and 151, entirely encased by the reservoir 62 and the cap 65, together cooperate to occlude the wet path 160. The cartridge 11 is fluidically isolated from the housing unit 12 in the storage state. The storage state of the pump 10 is a stable state that the pump 10 can be kept in for long periods of time. Since the reservoir 62 is sterilized and the cap 65 is separately sterilized, the cartridge 11 can be usefully maintained in the storage state of the pump 10 as long as the medicament does not expire.

The pump 10 is delivered to a health worker in the storage state, and the health worker then must ready the pump 10 for use. To do so, the health worker must first assemble the pump 10 into the ready state. This is shown in FIGS. 1A, 3A, 3B, and 3C. It is simple to arrange the pump 10 into the ready state. The health worker merely needs to apply the cartridge 11 to the housing unit 12. The worker registers the base 60 with the seat 32 at the top of the foot 31 of the housing unit 12. The worker applies the base 60 into the seat 32, seating it therein, and then pivots the rest of the cartridge 11 into the dock 30 of the housing unit 12, inserting the sensor 143 on the cap 65 into the slot 41 and the catch 142 into the smaller slot 42. The slot 144 in the catch 142 engages with the enlarged head of the tab 43, and the cartridge 11 is secured to the housing unit 12 if necessary. A push button release 161 on the outside of the housing unit 12 releases the capture of the cartridge 11 from the housing unit 12. Because the cartridge 11 is fluidically isolated from the housing unit 12, the cartridge 11 can be released at any time and discarded or moved to another housing unit 12 if needed.

The above steps describe the process for placing the pump 10 into the ready state from the storage state. The ready state is still stable for long-term storage, but is distinguished from the storage state because the cartridge 11 is now applied the housing unit 12. However, the upper and lower ribbons 150 and 15 are still disposed between the first and second gaskets 95 and 105. The occlusions of the upper and lower ribbons 150 and 151, still entirely encased by the reservoir 62 and the cap 65, still cooperate to occlude the wet path 160. The cartridge 11 is still fluidically isolated from the housing unit 12 in the ready state.

Figure 4A:
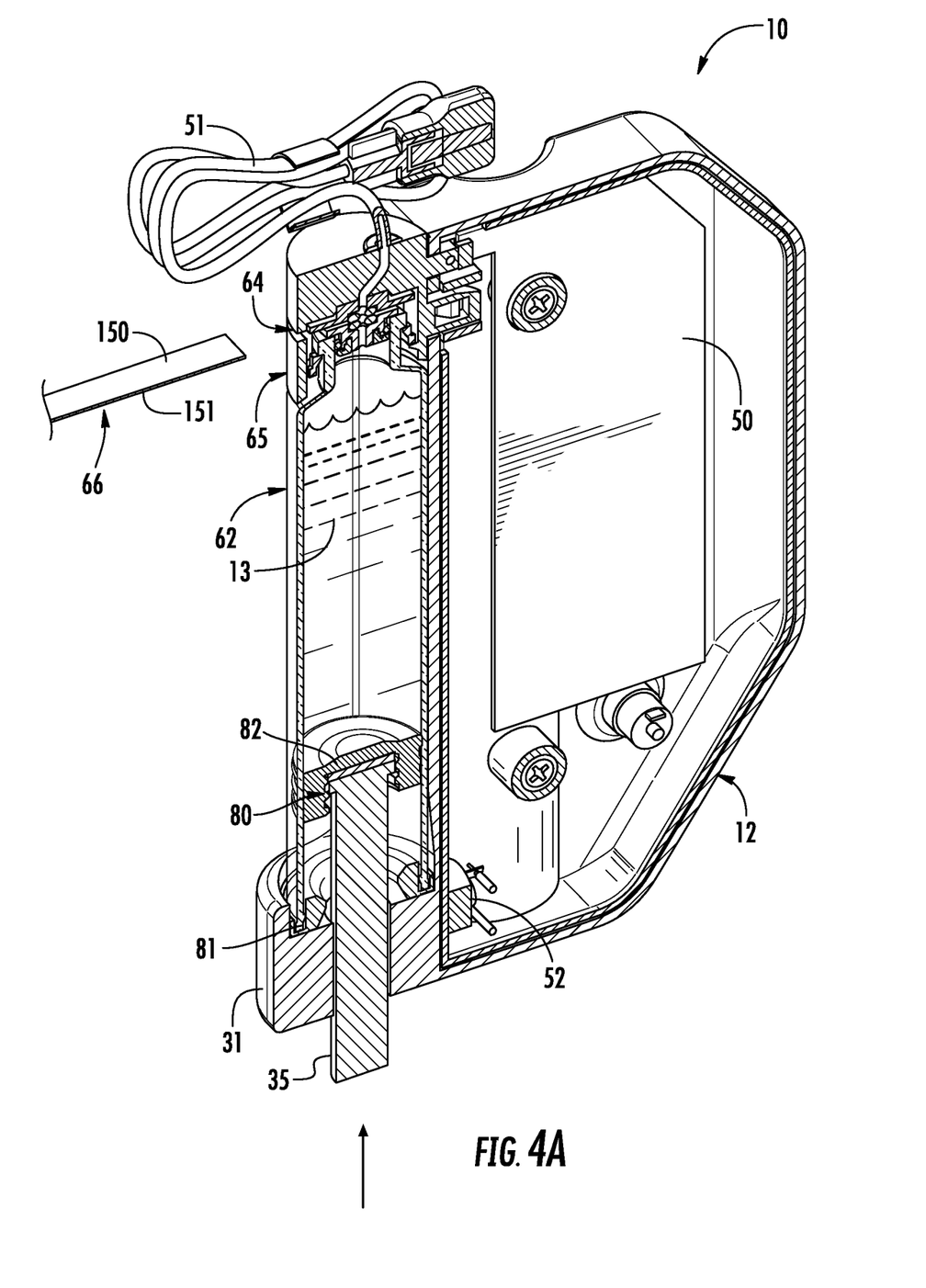
FIGS. 4A and 4B are section and enlarged section views, respectively, taken along the line 3-3 in FIG. 1A, showing the pump in the use state.
Figure 4B:
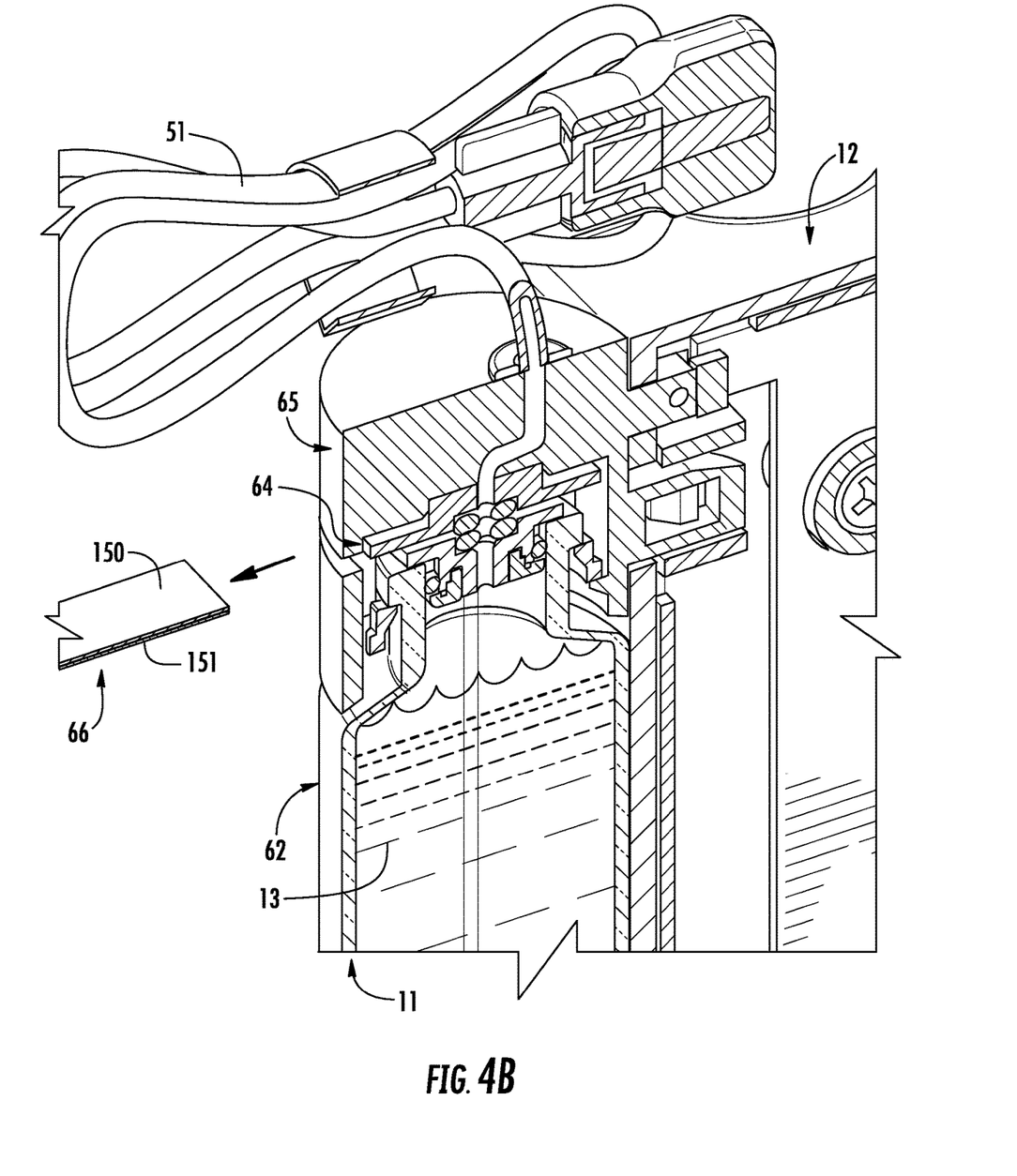

To arrange the pump 10 from the ready state to a use state, shown in FIGS. 4A and 4B, the health worker merely needs to remove the pull assembly 66. Removal of the pull assembly 66 removes the upper and lower ribbons 150 and 151 from the aseptic connector assembly 64, thereby removing the occlusions of the wet path 160 in the aseptic connector assembly 64. The gaskets 95 and 105, under the compressive force of the upper aseptic connector 83 against the lower aseptic connector 84, are now compressed directly against each other in continuous sealing contact, without the occlusions of the upper and lower ribbons 150 and 151 between. Since the gaskets 95 and 105 are maintained in coaxial alignment, they register with each other to form a fluid-impermeable seal and prevent any liquid from leaking between the gaskets, thus ensuring that the wet path 160 is fluidically isolated and protected from both leaking and ingress contamination. The wet path 160 is thus opened for communication of fluid medicament from the reservoir 62 to the conduit 140 in the cap 65. The cartridge 11 is still fluidically isolated from the housing unit 12 in the use state, however.

Though medicament can flow from the reservoir 62 to the conduit 140, it does not flow until the pump 10 is energized and the plunger rod 35 is advanced. The health worker must first connect the pump 10 to the patient. The health worker may arrange the pump 10 for use, such as by hanging it from a hook on a stand proximate to the patient. The health worker couples the fitting on the administration line 51 to the outlet 141 and then removes the cap on the other end of the administration line 51. The administration line 51 may be connected to a catheter, an intravenous line, a port connected to the patient, or some other part of an intravenous line system. The health worker next activates the pump 10 on and inputs dosing information. The health worker uses the control buttons 46 to do this, depressing the control buttons 46 until the desired settings are selected, as confirmed on the display 45. In some circumstances, the pump 10 may be primed to remove any air from the wet path 160.

Figure 5:
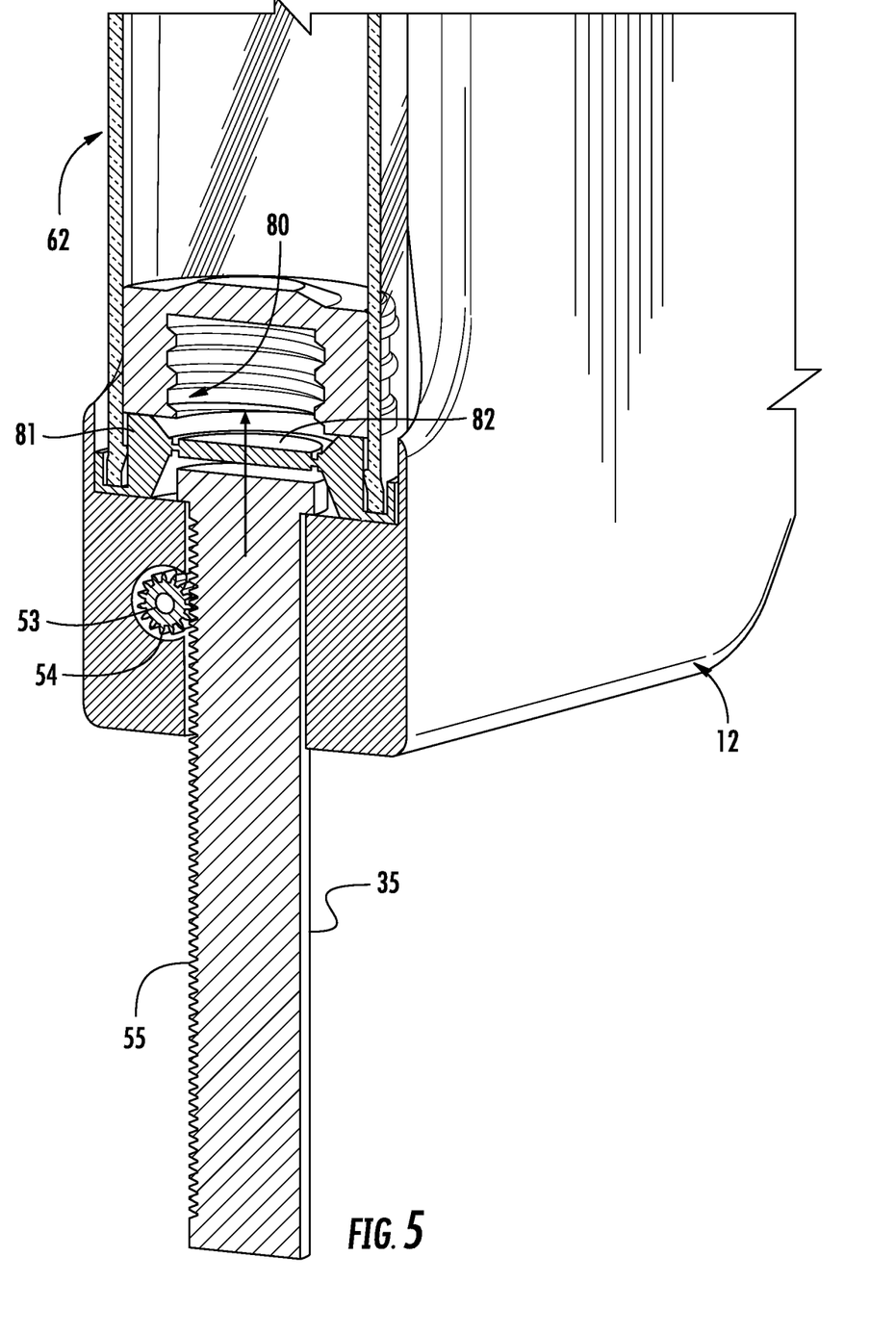
FIG. 5 is a section view taken along the line 5-5 in FIG. 1A.

The health worker then starts the pump 10 to dispense the fluid medicament 13 by depressing one of the control buttons 46. Logic controllers on the PCB 50 transmit power, supplied by a battery behind the PCB 50, to a motor 52, which is electrically coupled to the PCB 50. The motor has a shaft 53 (seen in FIG. 5) on which a pinion gear 54 is mounted. The pinion gear 54 is engaged with teeth 55 formed along one side of the plunger rod 35. When the motor 52 receives power, the pinion gear 54 rotates and advances the plunger rod 35 upward. The plunger rod 35 moves upward and encounters the central barrier 82 of the base 60. The central barrier 82 is formed integrally to the outer ring 81, but at its periphery, the central barrier 82 is thinned (as seen best in FIG. 5) to provide a stress point. Once the plunger rod 35 encounters the central barrier 82 and continues to advance, the plunger rod 35 moves through the central barrier 82, severing it from the outer ring 81. The plunger rod 35 tampers the reservoir 62, as severing of the central barrier 82 indicates that some of the medicament 13 may have been dispensed or something may have interfered with the medicament 13. The central barrier 82 is thus torn from the outer ring and is carried upward atop the plunger rod 35, as seen in FIG. 4A. However, because the plunger rod 35 has not yet reached the bottom of the plunger 61, medicament has yet to begin to flow from the reservoir 62 through the conduit 140 and into the administration line 51.

The plunger rod 35 advances into the socket 80 of the plunger 61. The central barrier 82 becomes disposed between the top of the plunger rod 35 and the underside of the socket 80. The motor 52 drives the plunger rod 35 upward at a predetermined rate corresponding to the appropriate dosage for the patient, displacing the medicament 13 from the reservoir 62, through the wet path 160, and out through the administration line 51. This continues until the reservoir 62 is emptied or the health worker discontinues administration of the medicament. The cartridge 11 is then ejected from the housing unit by depressing the push button release 161, which releases the catch 142, and the cartridge 11 is disposed. The housing unit 12 is available to be re-used with a new cartridge 11.

A preferred embodiment is fully and clearly described above so as to enable one having skill in the art to understand, make, and use the same. Those skilled in the art will recognize that modifications may be made to the description above without departing from the spirit of the invention, and that some embodiments include only those elements and features described, or a subset thereof. To the extent that modifications do not depart from the spirit of the invention, they are intended to be included within the scope thereof.

The invention claimed is:

1. A pump comprising:
   a housing unit, a reservoir filled with a fluid and applicable to the housing unit, and a cap fit on the reservoir, wherein the reservoir includes an open top, an open bottom, and a sidewall that decreases in diameter at a neck terminating in a mouth;

the cap includes a body with a closed top of the cap, an open bottom of the cap, an interior cavity extending from the open bottom of the cap into the body to an upper surface formed with a depression therein, and a conduit extending from the interior cavity to the top of the cap, wherein the body of the cap is fit on the reservoir in an overlapping fashion such that the open bottom of the cap encircles the neck of the reservoir and the neck and the mouth of the reservoir are disposed within the interior cavity;

an aseptic connector assembly comprising a first portion snug fit in the depression of the upper surface of the cap and having a first occlusion opposite the depression, and a separate second portion held against the mouth of the reservoir and having a second occlusion, a collar extending into the reservoir, and a second annular gasket compressed laterally between the collar and the mouth of the reservoir;

a pull assembly extending from within the aseptic connector assembly, where the pull assembly forms the first and second occlusions, and through a slot in the cap to outside the reservoir and the cap;

a storage state of the pump, in which the reservoir is separate from the housing unit, and the first and second occlusions are entirely encased by the reservoir and the cap and together cooperate to occlude a wet path extending from the reservoir through the conduit in the cap;

a ready state of the pump, in which the reservoir is applied to the housing unit and the first and second occlusions are entirely encased by the reservoir and the cap and cooperate to occlude the wet path; and a use state of the pump, in which the reservoir is applied to the housing unit, the first and second occlusions are removed from the first and second portions of the aseptic connector assembly, and the wet path is opened for communication of the fluid from the reservoir to the conduit in the cap;

wherein removal of the pull assembly removes the first and second occlusions from the first and second portions of the aseptic connector assembly, and arranges the pump from the ready state to the use state.

2. The pump of claim 1, wherein:
the first portion of the aseptic connector assembly includes a first annular gasket which is compressed toward the second annular gasket; and
in each of the storage and ready states, the first and second occlusions are between the first and second annular gaskets.

3. The pump of claim 2, wherein in the use state, the first and second annular gaskets are against each other in continuous sealing contact.

4. The pump of claim 2, wherein:
the first and second portions of the aseptic connector assembly are each formed with a bore and a seat around the respective bore; and
the first and second annular gaskets are each seated in the seat of the respective first and second portions.

5. The pump of claim 1, further comprising:
a plunger within the reservoir;
a plunger rod in the housing unit, wherein the plunger rod is operatively coupled to a motor in the housing unit to be driven into the plunger and through the reservoir in response to operation of the motor;

a tamper-evident base of the reservoir having a frangible central barrier, the frangible central barrier configured to sever in response to the plunger rod moving therethrough; and
the plunger rod tampers the reservoir when the frangible central barrier is severed from the tamper-evident base.

6. The pump of claim 5, wherein:
the tamper-evident base includes a rigid outer ring to which the frangible central barrier is attached; and
the frangible central barrier spans within the outer ring.

7. The pump of claim 1, wherein the fluid is selected from a group consisting of acetaminophen, ketamine, propofol, dexmedetomidine, fentanyl, remifentanyl, etomidate, midazolam, foscarnet, ganciclovir, dopamine, dobutamine, milrinone, hemin, bupivacaine, ropivacaine, lidocaine, ciprofloxacin, cefazolin, fluconazole, cefmetazole, nafcillin, zoledronic acid, hetastarch, lactated ringers, hydroxyethyl starch, sodium chloride, dextrose, bendamustine, filgrastim, aztreonam, 5-fluorouracil, cetuximab, bortezomib, epirubicin, fludarabine, irinotecan, oxalaplatin, paclitaxel, carboplatin, cisplatin, cytarabine, methotrexate, vinblastine, vincristine, and ifosfamide.

8. A pump comprising:
a housing unit, a separate reservoir which is separable from but applicable to the housing unit, and a cap fit on the reservoir, wherein the reservoir includes an open top, an open bottom, and a sidewall that decreases in diameter at a neck terminating in a mouth;

the cap includes a body with a closed top of the cap, an open bottom of the cap, an interior cavity extending from the open bottom of the cap into the body to an upper surface formed with a depression therein, and a conduit extending from the interior cavity to the top of the cap, wherein the body of the cap is fit on the reservoir in an overlapping fashion such that the open bottom of the cap encircles the neck of the reservoir and the neck and the mouth of the reservoir are disposed within the interior cavity of the cap;

an aseptic connector assembly comprising a first portion snug fit in the depression of the upper surface of the cap and having a first occlusion opposite the depression, and a separate second portion held against the mouth of the reservoir and having a second occlusion, a collar extending into the reservoir, and a second annular gasket compressed laterally between the collar and the mouth of the reservoir;

a wet path extending from the reservoir to and through the conduit but occluded by the first and second occlusions; and a pull assembly extending from within the aseptic connector assembly, where the pull assembly forms the first and second occlusions, and through to a slot to outside the reservoir and the cap;

wherein the pull assembly is removable from the aseptic connector assembly to remove the first and second occlusions from the first and second portions of the aseptic connector assembly, thereby opening the wet path from the reservoir to the conduit.

9. The pump of claim 8, wherein:
the first portion of the aseptic connector assembly includes a first annular gasket, and the first and second annular gaskets are compressed toward each other; and
the first and second occlusions are between the first and second annular gaskets until the pull assembly is removed from the aseptic connector assembly.

10. The pump of claim 9, wherein when the pull assembly is removed from the aseptic connector assembly, the first and second annular gaskets are brought against each other in continuous sealing contact.

11. The pump of claim 9, wherein:
the first and second portions of the aseptic connector assembly are each formed with a bore and a seat around the respective bore; and
the first and second annular gaskets are each seated in the seat of the respective first and second portions.

12. The pump of claim 8, further comprising:
a plunger within the reservoir;
a plunger rod in the housing unit, wherein the plunger rod is operatively coupled to a motor in the housing unit to be driven into the plunger and through the reservoir in response to operation of the motor;
a tamper-evident base of the reservoir having a frangible central barrier, the frangible central barrier configured to sever in response to the plunger rod moving therethrough; and
the plunger rod tampers the reservoir when the frangible central barrier is severed from the tamper-evident base.

13. The pump of claim 12, wherein:
the tamper-evident base includes a rigid outer ring to which the frangible central barrier is attached; and
the frangible central barrier spans within the outer ring.

14. A pump comprising:
a housing unit holding a motor;
a cartridge separate from but applicable to the housing unit, the cartridge including a reservoir, a cap fit on the reservoir, an outlet of the cap, and an aseptic connector assembly disposed between the reservoir and the cap to govern movement of a fluid in the reservoir along a wet path extending from the reservoir to the outlet;
the reservoir includes an open top, an open bottom, and a sidewall that decreases in diameter at a neck terminating in a mouth;
the cap includes a body with a closed top of the cap, an open bottom of the cap, an interior cavity extending from the open bottom of the cap into the body to an upper surface formed with a depression therein, and a conduit extending from the interior cavity to the top of the cap, wherein the body of the cap is fit on the reservoir in an overlapping fashion such that the open bottom of the cap encircles the neck of the reservoir and the neck and the mouth of the reservoir are disposed within the interior cavity of the cap;
the aseptic connector assembly comprises a first portion snug fit in the depression of the upper surface of the cap and having a first occlusion, and a separate second portion held against the mouth of the reservoir and having a second occlusion, a collar extending into the reservoir, and a second annular gasket compressed laterally between the collar and the mouth of the reservoir;
three states of the pump, including:
a storage state, in which the cartridge is free of the housing unit;
a ready state, in which the cartridge is applied to the housing unit and the wet path is occluded by the first and second occlusions; and
a use state, in which the cartridge is applied to the housing unit, the first and second occlusions are removed from the first and second portions of the aseptic connector assembly, and the wet path is opened for communication of the fluid from the reservoir out the outlet of the cap.

15. The pump of claim 14, further comprising a pull assembly extending from within the aseptic connector assembly where the pull assembly forms the first and second occlusions to outside the reservoir and the cap, wherein removal of the pull assembly removes the first and second occlusions from the first and second portions of the aseptic connector assembly and arranges the pump from the ready state to the use state.

16. The pump of claim 14, wherein:
the first portion of the aseptic connector assembly includes a first annular gasket, and the first and second annular gaskets are compressed toward each other; and
in each of the storage and ready states, the first and second occlusions are between the first and second annular gaskets.

17. The pump of claim 16, wherein in the use state, the first and second annular gaskets are against each other in continuous sealing contact.

18. The pump of claim 16, wherein:
the first and second portions of the aseptic connector assembly are each formed with a bore and a seat around the respective bore; and
the first and second annular gaskets are each seated in the seat of the respective first and second portions.

19. The pump of claim 14, further comprising:
a plunger within the reservoir;
a plunger rod in the housing unit, wherein the plunger rod is operatively coupled to the motor in the housing unit to be driven into the plunger and through the reservoir in response to operation of the motor;
a tamper-evident base of the reservoir having a frangible central barrier, the frangible central barrier configured to sever in response to the plunger rod moving therethrough; and
the plunger rod tampers the reservoir when the frangible central barrier is severed from the tamper-evident base.

20. The pump of claim 19, wherein:
the tamper-evident base includes a rigid outer ring to which the frangible central barrier is attached; and
the frangible central barrier spans within the outer ring.

* * * * *